(12) United States Patent
Maev et al.

(10) Patent No.: US 11,213,207 B2
(45) Date of Patent: Jan. 4, 2022

(54) DEVICE AND METHOD USING DAMPED HARMONIC ANALYSIS FOR AUTOMATED PULMONARY AND ABDOMINAL EXAMINATION

(71) Applicant: UNIVERSITY OF WINDSOR, Windsor (CA)

(72) Inventors: Roman Maev, Windsor (CA); Eugene Malyarenko, Troy, MI (US); Mircea Pantea, Windsor (CA); Fedar M. Seviaryn, Windsor (CA)

(73) Assignee: UNIVERSITY OF WINDSOR, Windsor (CA)

( * ) Notice: Subject to any disclaimer, the term of this patent is extended or adjusted under 35 U.S.C. 154(b) by 708 days.

(21) Appl. No.: 15/735,592

(22) PCT Filed: Jun. 8, 2016

(86) PCT No.: PCT/CA2016/000168
§ 371 (c)(1),
(2) Date: Dec. 11, 2017

(87) PCT Pub. No.: WO2016/097232
PCT Pub. Date: Dec. 15, 2016

(65) Prior Publication Data
US 2019/0223726 A1    Jul. 25, 2019

Related U.S. Application Data

(60) Provisional application No. 62/174,496, filed on Jun. 11, 2015.

(51) Int. Cl.
*A61B 5/08* (2006.01)
*A61B 5/00* (2006.01)
(Continued)

(52) U.S. Cl.
CPC .......... *A61B 5/0051* (2013.01); *A61B 5/0057* (2013.01); *A61B 5/08* (2013.01);
(Continued)

(58) Field of Classification Search
CPC ....... A61B 5/0051; A61B 5/0057; A61B 5/08; A61B 5/0803; A61B 5/4238;
(Continued)

(56) References Cited

U.S. PATENT DOCUMENTS 5,006,984 A * 4/1991 Steele .................... A61B 5/417
600/587
5,579,771 A    12/1996 Bonnefous
(Continued)

FOREIGN PATENT DOCUMENTS

WO    2003096872 A2    11/2003
WO    2003096872 A3    11/2003

OTHER PUBLICATIONS

Canadian IP Office; International Preliminary Report on Patentability prepared by International Searching Authority for correlating PCT Application No. PCT/CA2016/000168, 6 pgs, (dated Dec. 12, 2017).
(Continued)

*Primary Examiner* — Navin Natnithithadha
(74) *Attorney, Agent, or Firm* — Womble Bond Dickinson (US) LLP

(57) ABSTRACT

An analyzer for diagnosing pulmonary and abdominals including, a pulsed force generator for outputting a mechanical disturbance to generate vibrations and reflected/return waves/vibrations in a patient's torso, and sensors for detecting the vibration/return wave signals. The apparatus compares the detected electrical signals with pre-stored reference wave profiles and based on the compared data
(Continued)

generates an output signal indicative of a potential presence or absence of a pulmonary disease and/or condition.

10 Claims, 11 Drawing Sheets

(51) Int. Cl.
    *A61B 7/00*     (2006.01)
    *A61B 9/00*     (2006.01)
    *G16H 50/20*     (2018.01)
(52) U.S. Cl.
    CPC .......... *A61B 5/0803* (2013.01); *A61B 5/4238* (2013.01); *A61B 5/4887* (2013.01); *A61B 5/7203* (2013.01); *A61B 5/7246* (2013.01); *A61B 5/7264* (2013.01); *A61B 5/7282* (2013.01); *A61B 5/742* (2013.01); *A61B 5/7405* (2013.01); *A61B 9/00* (2013.01); *G16H 50/20* (2018.01); *A61B 7/00* (2013.01); *A61B 2560/0431* (2013.01)
(58) Field of Classification Search
    CPC ... A61B 5/4887; A61B 5/7203; A61B 5/7246; A61B 5/7264; A61B 5/7282; A61B 5/7405; A61B 5/742; A61B 9/00; A61B 7/00; A61B 2560/0431; G16H 50/20
    USPC .......................................... 600/484, 529–543
    See application file for complete search history.

(56) References Cited

U.S. PATENT DOCUMENTS

| | | |
|---|---|---|
| 5,638,823 A | 6/1997 | Akay |
| 7,533,758 B1 | 5/2009 | French |
| 2003/0220556 A1 | 11/2003 | Porat |
| 2004/0214348 A1 | 10/2004 | Nicholson |
| 2005/0065426 A1 | 3/2005 | Porat et al. |
| 2006/0217640 A1 | 9/2006 | Trandafir |
| 2010/0191110 A1 | 6/2010 | Insana |
| 2011/0004104 A1* | 1/2011 | Sandrin ................ A61B 5/6885 600/459 |
| 2013/0281897 A1 | 10/2013 | Hoffmann |

OTHER PUBLICATIONS

Canadian IP Office; International Search Report by International Searching Authority for correlating PCT Application No. PCT/CA2016/000168, 6 pgs, (dated Sep. 14, 2016).
Canadian IP Office; The Written Opinion by International Searching Authority for correlating PCT Application No. PCT/CA2016/000168, 5 pgs, (dated Sep. 14, 2016).

* cited by examiner

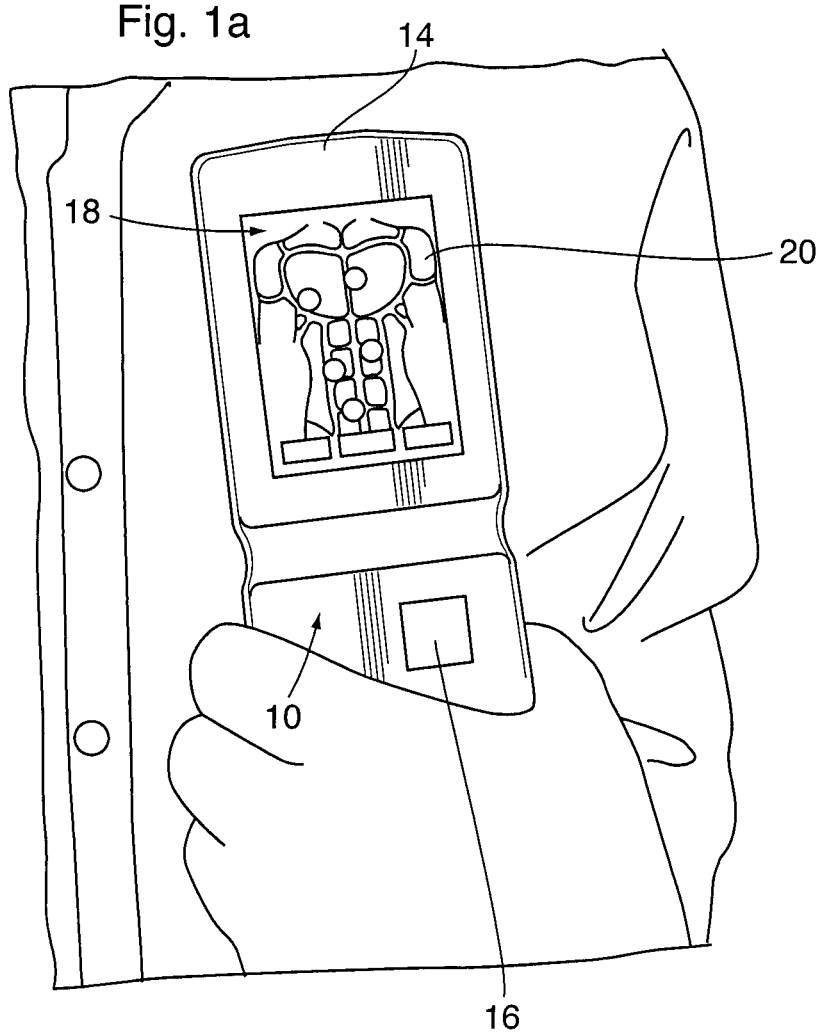
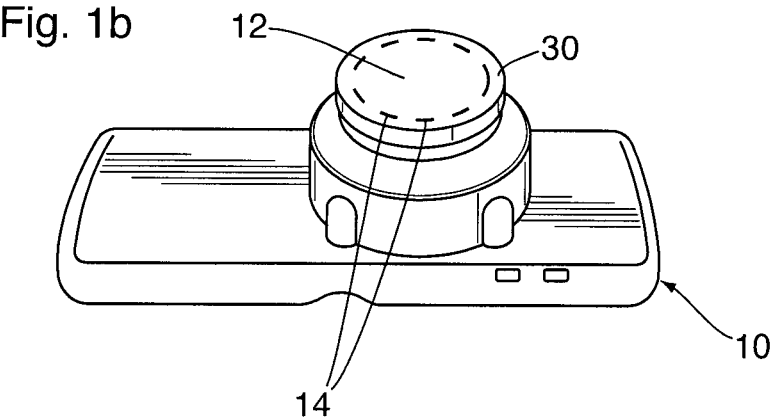

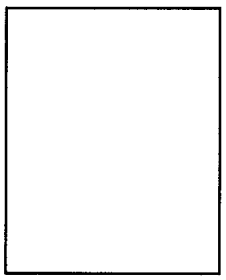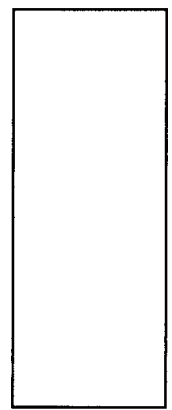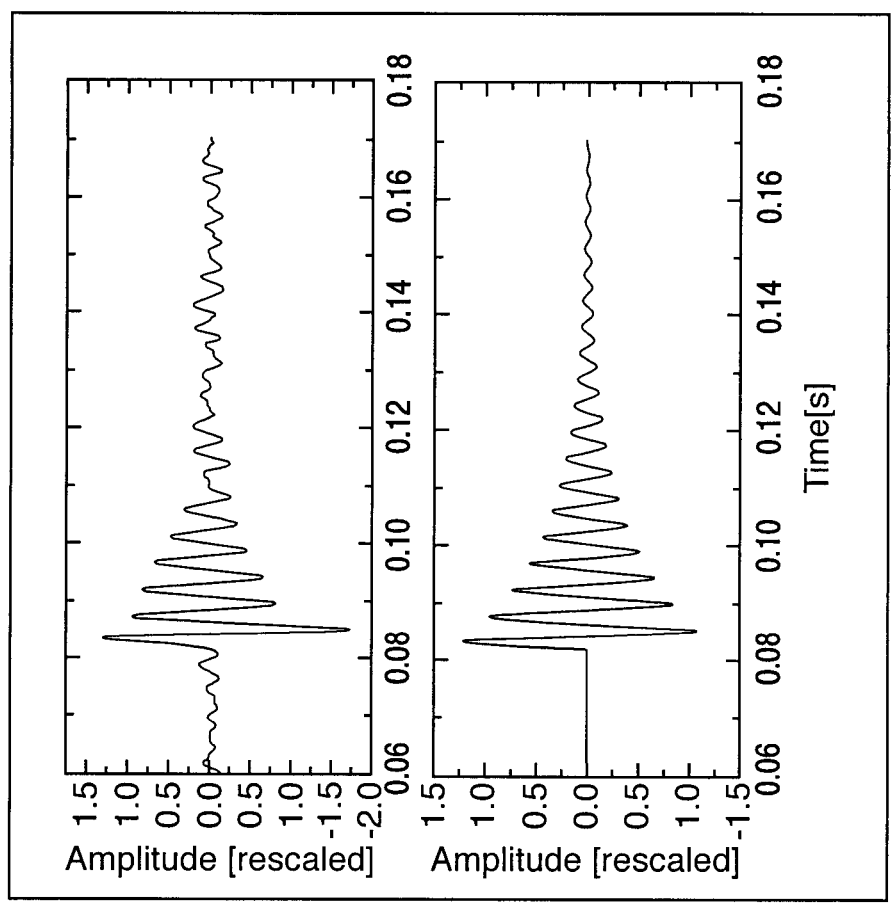
Fig. 12

DEVICE AND METHOD USING DAMPED HARMONIC ANALYSIS FOR AUTOMATED PULMONARY AND ABDOMINAL EXAMINATION

CROSS-REFERENCE TO RELATED APPLICATIONS

This patent application is a U.S. National Phase application under 35 U.S.C. § 371 of International Application No. PCT/CA2016/000168, filed 8 Jun. 2016, entitled DEVICE AND METHOD USING DAMPED HARMONIC ANALYSIS FOR AUTOMATED PULMONARY AND ABDOMINAL EXAMINATION, which claims priority and the benefit of 35 U.S.C. § 119(e) to U.S. Provisional Patent Application Ser. No. 62/174,496, filed 11 Jun. 2015, the entirety of which was incorporated herein by reference.

TECHNICAL FIELD

The present invention relates generally to the medical diagnostics field, and more specifically to a method and apparatus for using the analysis of clinical percussion signals, preferably tympanic or resonant energy reflected wave energy, and preferably damped harmonic analysis, for automated pulmonary and/or abdominal examination or diagnosis in the medical diagnostics field.

BACKGROUND OF THE INVENTION

All objects have the capability of absorbing, transmitting and reflecting sound waves. The ability for objects to vibrate under impact is dependent on the material makeup, configuration, shape and size of the object and these characteristics will affect how these objects behave with different frequencies of sound both within and outside the human hearing range. It is also well known that low frequencies penetrate deeper; travel further; penetrate a wider range of materials; and go through more objects than higher frequencies. Further, the reflected wave from a low frequency source is less complex than that of a higher frequency wave. Although the low frequency wave is less complex it does significantly change with even subtle changes in the object, and which is quite obvious in the shape and form of the reflected wave.

The absorption and reflection of wave energy has been used by medical practitioners as a diagnostic tool in the identification of a number of different pulmonary and/or abdominal conditions. In particular, the analysis of soundwaves produced by percussion on boney areas of a patient's torso, such as the clavicle, has long been used to identify lung lesions which may be indicative of tuberculosis. It has been recognized that conventional pulmonary diagnostics technologies, such as chest X-Ray and X-Ray CT, are not easily adaptable for the rapid, cost-effective deployment at the point of first contact with an injured patient or party in distress, outside of the clinical setting. Similarly, the established traditional examination technique of clinical percussion (manual tapping on the body parts and listening for differences in the produced sound) is not well suited for the field conditions.

Typically, percussion is provided as part of or in parallel with an auscultation procedure wherein the practitioner, using a stethoscope or his own ear, identifies by professional skill tympanic reflective or resonant sounds produced in a patient's torso or abdomen which are indicative of a potentially underlying medical condition or malady.

The use of manual percussion in medical diagnosis is further subject to inherent inaccuracies in that it is to a significant extent reliant on the individual skill and acumen of the medical practitioner. In addition, manual percussion as a diagnostic tool may be poorly suited where a diagnosis is needed under less than ideal conditions, and for example if diagnosis is to be performed by medical practitioners, medics and/or first responders in the field, as for example at the site of traffic accidents or under battlefield conditions.

SUMMARY OF THE INVENTION

In one non-limiting object, the present invention seeks to provide an apparatus which is configured for use in identifying the existence of a potential pulmonary and/or abdominal conditional or abnormality in a patient, and which seeks to minimize the variability of results attributed to the individual practitioner skill associated with manual percussion diagnostic procedures.

In one embodiment, the invention provides a diagnostic apparatus or analyzer, and most preferably a portable diagnostic analyzer which is operable to provide an indication of either the presence or absence of a potential pulmonary and/or abdominal condition in a patient. Such conditions may include without limitation, the presence of a disease or infection, an indication of potential internal bleeding, organ or bone trauma, the presence of masses including gallstones and kidney stones, foreign objects or hardened tissues, the presence of air in the pleural space as in pneumothorax, the presence of liquid in the chest cage as in hydro/hemothorax or pleural effusion, the presence of air/liquid in the abdominal cavity, and the like.

In a simplified construction, the apparatus includes a pulsed force generator which is operable to transmit or output to a selected patient target area, a percussion or a mechanical disturbance in the form of a pulse force. The apparatus is provided with one or more sensors which are operable to sense the waves and/or vibrations induced by percussion. Such sensors may include one or more of acoustic sensors, such as air microphones, contact microphones, accelerometers, acoustic transducers, contact pressure sensors, as well as touch sensors and which are operable to detect surface vibrations and/or return pressure waves in the form of auditory and/or elastic waves. Based on the detected surface vibration and/or return wave properties, the analyzer preferably operates to generate an output audio and/or video display signal to the user providing an indication of the presence or absence of a potential pulmonary disease and/or other patient condition.

Preferably the diagnostic apparatus is provided with a processor which is operable to classify the type of sensed data and/or output signal (here and after collectively an output signal) provided by the analyzer. Such classification may be based upon one or more properties of the pulse force initially output and/or the sensed direct and return energy waves, and which for example may include without restriction, one or more of the site selection of the target area, the energy and/or frequency of the initial output pulsed force, the energy wave amplitude of the detected resulting tympanic or return waves and/or vibrations energy waves, the phase and/or frequency of one or more detected return waves and/or vibrations and/or the damping coefficient of the detected return waves and/or vibrations. Preferred classifications could for example include without restriction, the classification of detected return energy as one or more of tympanic; hyperresonant; normal resonant; impaired resonant; dull (consolidation); or stony.

More preferably, the processor may be operable to further classify and/or generate output signals indicative of the presence or absence of a particular disease or condition on the basis of additional input patient-specific parameters. Such input parameters could include without restriction, one or more of the patient's age, sex, weight, smoker status, and/or previously identified physical impairments or conditions.

In a simplified construction, the apparatus is provided with a reciprocally moveable piston and/or hammer which may be selectively moved to provide a strike or impact force at the patient's target area. In a simplified construction, the apparatus may be provided with an electro-mechanically displaceable piston which is adapted to be moved between a forward impact position, where the piston is moved into physical contact with a target area of interest on a patient's torso, chest and/or abdomen, and a retracted position spaced therefrom. In this construction, the kinetic energy of the moving impactor is converted to the desired pulsed force at the moment of impact. Such conversion is more preferably facilitated by introducing an intermediate plate (plessimeter) between the impactor and the human body. The plessimeter protects the body from injury by the impactor and also standardizes the impact conditions, e.g. force and duration, to maintain repeatability.

In another simplified construction, the desired pulsed force may be produced by means of electromechanical or other type of energy conversion without using kinetic energy of a moving impactor. In this construction, the plunger stays in contact with the patient's body or plessimeter and exerts the pulsed force when current flows through the surrounding coil (Lorentz force), a voltage is applied to the capacitor (electrostatic force) or other excitation mechanisms take place. It is to be appreciated, however, that other mechanisms to impart the desired output energy at a specific target area may also be used. By way of non-limiting example, other apparatus for generating and imparting the output pulsed force could include without restriction, a rotating pawl hammer construction, as well as valve gas nozzles which are operable to emit a selected compressed gas pressurized gas flow or burst against the target area.

Most preferably, the analyzer is operable to apply to a number of predefined patient target areas, an associated preselected output pulsed force, and which most preferably may be varied having regard to the specific target area of diagnosis and/or the particular potential patient medical condition of concern.

The operation of the analyzer and the associated technology is based on the sensing and identification of acoustic characterizations of low frequency waves/vibrations generated in the patient's body, and which are preferably at a frequency of between about 20 Hz and 1000 Hz, preferably between about 20 Hz and 300 Hz, and most preferably between about 20 Hz and 100 Hz. The analyzer further may operate by comparing such readings with data representative of their one or more readings representing normal or desired states, and/or with pre-stored or modelled data representative of normal, stressed, compromised or injured states (depending on the application). In one embodiment, based on the divergence of a detected or reflected waveform from a pre-identified normal or desired waveform, the apparatus is operable to conduct an analysis to determine a likely injury, disease, condition or other cause for any detected divergence. More preferably, the device may operate to provide direction as to what may be done so as not to compound or even to correct the situation or condition.

In one non-limiting medical example, patient pulmonary traumas such as pneumothorax and/or hydrothorax may result from an accident via a chest impact or penetrating wound, or may also occur in battlefield environments. Pulmonary conditions may also develop chronically without a known point of onset. The present apparatus may preferably be used "in-field" at the site of an accident to provide fast and accurate diagnosis of such trauma and/or conditions may be advantageous and may even be life-saving.

More preferably the invention provides a portable battery-powered hand held function analyzer which is adapted for in-field uses at the first point of patient contact. The diagnostic analyzer allows for potential pulmonary traumas such as pneumo- and hemothorax to be identified rapidly and on the site by emergency first responders such as military medics, paramedics and ambulance personnel, thus allowing for patient pre-stabilization or the re-focusing on other activities, issues and conditions affecting the patient. In an alternate embodiment, the invention provides an apparatus and method for the automated detection and/or identification of other pulmonary or other abdominal conditions, such as lung and other traumas as quickly and early as possible.

In another possible construction, the pulmonary function analyzer is provided with a graphic display which allows for the output of visual user instructions, and which include without restriction target area placement, trauma/condition identification, and possible treatment or triage. The apparatus is adapted to impart at a target area of the patient's chest cavity and/or abdomen an input pulsed force. The analyzer sensors are most preferably located at or adjacent the target area in a position to detect and convert to electric signals, surface vibrations and/or reflected waves which are produced from portions of the input wave reflecting from and/or transmitting through barrier surfaces produced by the patient's tissues, internal organs, and/or bones.

An analyzer processor compares the waveforms and frequency spectra of one or more sensed vibrations and/or reflected return energy waves, and/or optionally the initial pulsed force output by the analyzer. Most preferably, the apparatus operates to identify and compare low frequency spectra of sensed vibrations and/in reflected or generated waves in the range of from less than about 1000 Hz, preferably from about 20 Hz to 300 Hz, and most preferably from about 20 Hz to 100 Hz. Other frequency spectra could also be used. The sensed waveforms are preferably assessed to identify whether or not the detected wave profile deviates from one or more predetermined profiles by a threshold amount indicative of an identified medical anomaly. Most preferably, a number of different predetermined profiles are stored in analyzer memory, and which are representative of normal and/or abnormal conditions. Such preselected profiles may include without limitation those representative of the occurrence of an internal physical trauma for selected types of bones, organs and/or soft tissue, including but not limited to pneumothorax, hydro/hemothorax, and pleural effusion, the presence of bacterial infection or infectious diseases such as tuberculosis, pulmonary hypertension or chronic obstruction, lung carcinoma, kidney stones, and the occurrence of abnormal fluid levels and/or internal bleeding.

Accordingly, the present invention resides in a number of non-limiting aspects and which include:
1. An analyzer for diagnosing a pulmonary and/or abdominal condition of a patient, the analyzer comprising, a pulsed force generator operable to generate and transmit to a target area of the patient at least one preselected output pulsed force, each said output pulsed force being selected to generate at the target area at least one associated surface vibration or reflected return energy wave, a sensor assembly for detecting the at least one surface vibration or return energy wave at said target area, and converting detected energy thereof into electrical signals, memory containing stored data representative of pre-stored wave profiles indicative of the presence and/or absence of one or more pulmonary and/or abdominal conditions, a processor containing programme instructions, whereby said processor is operable to, compare data representative of the detected energy of at least a part of the at least one associated return energy wave generated with said stored data representative of at least one said pre-stored energy wave profiles and based on the compared data generate an output signal indicative of a potential presence or absence of a pulmonary disease and/or condition in said patient.

2. An apparatus or analyzer for diagnosing a pulmonary or abdominal condition of a patient, the apparatus comprising, a pulsed force generator operable to generate and impart on a target area of the patient's torso a preselected output pulsed force, the input pulsed force being selected to generate in said patient's torso associated reflected return energy waves, a sensor assembly for detecting said return energy waves at said target area, and converting said return energy waves into sensed data signals, and a processing assembly having memory, a processor, and programme instructions, whereby said processor is operable to, perform damped harmonic analysis on said sensed data signals to identify a damped harmonic signal, and compare at least part of the sensed data signals with data representative of at least one of the output energy of said pulsed force generator and data stored in memory representative of one or more return energy wave profiles representative of a pre-identified pulmonary or abdominal condition or state, based on the compared data, generate an audible and/or visual output signal indicative of the presence or absence of a pulmonary disease or condition in said patient.

3. A portable diagnosis analyzer for diagnosing a pulmonary function of a patient, the analyzer including, a display, a pulsed force generator operable to generate and transmit to a target area of the patient's torso a preselected output pulsed force selected to generate at said target area associated return waves/vibrations, a sensor assembly operable to detect energy of said return waves/vibrations at said target area and convert such detected energy into sensed data signals, and a processing assembly including memory and a processor containing programme instructions, said processor is operable to, perform damped harmonic analysis on at least part of said sensed data signals to generate a damped harmonic signal, and compare the damped harmonic signal with preselected harmonic signals stored in said memory, said preselected harmonic signals being representative of a pre-identified pulmonary state, disease or condition, and based on said comparison, generate an output a signal to a user indicative of the potential presence or absence of a pulmonary disease and/or condition in said patient.

An analyzer in accordance with any of the preceding or hereafter described aspects, wherein said processor includes pre-stored software comprising programme instructions operable to compare data representative of an output energy of said output pulsed force and the data representative of the detected energy, and perform damped harmonic analysis on at least one of said data representative of said output energy and said data representative of said detected energy.

An analyzer in accordance with any of the preceding or hereafter described aspects, wherein the processor is operable to identify and select by at least one of signal filtering and signal truncation, an informative portion of the electrical signals as the part of the at least one associated return energy wave compared with said stored data.

An analyzer in accordance with any of the preceding or hereafter described aspects, wherein the informative portion of the detected energy is identified and selected by filtering the electrical signals based on pre-identified background patterns.

An analyzer in accordance with any of the preceding or hereafter described aspects, wherein the processor is operable to effect damped sinusoidal signal conditioning on data, representative of the detected energy of at least part of a plurality of said detected return energy waves; and output a classification of the detected energy as at least part of the output signal based on said signal conditioning.

An analyzer in accordance with any of the preceding or hereafter described aspects, wherein prior to damped harmonic analysis, the processor is operable to effect signal conditioning of the detected energy electrical signals by one or more steps selected from the group consisting of windowing the electrical signals, removing direct current (DC) offset from the electrical signals; and filtering preselected high and/or low frequency components from the electrical signals.

An analyzer in accordance with any of the preceding or hereafter described aspects, wherein said damped harmonic analysis comprises nonlinear spectral fitting of the detected waves of a plurality of said associated waves detected at the target area, with at least one of Lorentzian curves, Prony's method and Pisarenko method.

An analyzer in accordance with any of the preceding or hereafter described aspects, wherein said processor is operable to classify said output signal based on at least one return wave parameter selected from the group consisting of energy wave amplitude, phase, frequency and damping coefficient.

An analyzer in accordance with any of the preceding or hereafter described aspects, wherein said processor is further operable to effect classification of the output signal based on at least one input patient parameter selected from the group consisting of patient age, sex, weight, and smoker status.

An analyzer in accordance with any of the preceding or hereafter described aspects, wherein said pulsed force generator includes a selectively displaceable piston member which is movable between a forward position, where said piston member engages said target area to transmit said output pulsed force thereto, and a retracted position spaced therefrom.

An analyzer in accordance with any of the preceding or hereafter described aspects, wherein the output pulsed force comprises a pulsed impact force at said target area selected at between about 0.1 and 10N, preferably 0.2 to 5N, and most preferably 0.5 to 4N.

An analyzer in accordance with any of the preceding or hereafter described aspects, wherein said output pulsed force comprises a pulsed impact force having a repetition frequency selected between 0.1 and 10 hertz and the pulse duration selected between 0.001 and 10 seconds.

An analyzer in accordance with any of the preceding or hereafter described aspects, wherein said target area is selected from the group consisting of a chest area, a back area and an abdomen area of the patient.

An analyzer in accordance with any of the preceding or hereafter described aspects, wherein said analyzer comprises a portable hand-held pulmonary function tester for diagnosing a pulmonary injury or condition in said patient; said tester further comprising a portable power source for supplying electric power to said pulsed force generator and said sensor assembly, and an output display for displaying said output signal as a graphic output.

An analyzer in accordance with any of the preceding or hereafter described aspects, wherein said damped harmonic analysis comprises performing nonlinear spectral fitting of the sensed data signals with at least one of Lorentzian curves, Prony's method and Pisarenko method.

An analyzer in accordance with any of the preceding or hereafter described aspects, wherein said processor is operable to compare the identified damped harmonic signal with at least one said preselected return energy wave profiles representative of a pre-identified pulmonary disease or condition stored in memory, said processor further outputting said output signal as a classified signal based on one or more sensed energy wave parameters selected from the group consisting of energy wave amplitude, phase, frequency and damping coefficient.

An analyzer in accordance with any of the preceding or hereafter described aspects, wherein said pulsed force generator includes a selectively movable piston member which is reciprocally moveable between a forward position, where said piston member is moved into physical engagement with said target area to transmit said pulsed force thereto, and a retracted position wherein said piston member is moved rearwardly to a position spaced from said target area.

An analyzer in accordance with any of the preceding or hereafter described aspects, wherein the pulsed force generator includes a motor operable to effect pulsed movement of said piston member to generate a pulsed impact force at said target area selected at between about 0.1 and 10N, preferably about 0.2 to 5N, and more preferably from about 0.5 to 4N.

An analyzer in accordance with any of the preceding or hereafter described aspects, wherein said pulsed impact force has a repetition frequency selected between 0.1 and 10 hertz and the pulse duration selected between 0.001 and 10 seconds An analyzer in accordance with any of the preceding or hereafter described aspects, wherein said target area is selected from the group consisting of the patient's chest wall, stomach, a super-transpylonic planar region of the patient's back and a sub-transpylonic planar region of the patient's back.

An analyzer in accordance with any of the preceding or hereafter described aspects, wherein said apparatus comprises a portable hand-held pulmonary function analyzer, and further includes a portable power source for supplying electric power to said pulsed force generator, said sensor assembly, and said processing assembly.

An analyzer in accordance with any of the preceding or hereafter described aspects, wherein the processor is operable to identify by at least one of signal filtering and signal truncation, an informative portion of the sensed data signals as the part of the sensed data signals compared with the data stored in memory.

An analyzer in accordance with any of the preceding or hereafter described aspects, wherein the informative portion of the sensed data signals is identified by filtering the sensed data signals to remove pre-identified background features and/or patterns.

An analyzer in accordance with any of the preceding or hereafter described aspects, wherein prior to performing damped harmonic analysis, the processor is operable to effect signal conditioning of the sensed data signals by one or more steps selected from the group consisting of windowing the sensed data signals, removing direct current (DC) offset from the sensed data signals, and filtering preselected high and/or low frequency components from the sensed data signals.

An analyzer in accordance with any of the preceding or hereafter described aspects, wherein the processor is operable to identify by at least one of signal filtering and signal truncation, an informative portion of the sensed data signals as the part of the sensed data signals compared with the data stored in memory.

An analyzer in accordance with any of the preceding or hereafter described aspects, wherein said processor is further operable to compare data representative of the output energy of said pulsed force generator, and the sensed data signals, and wherein the identification of the informative portion is based in part on said comparison.

An analyzer in accordance with any of the preceding or hereafter described aspects, wherein said damped harmonic analysis comprises nonlinear spectral fitting of the informative portions of the sensed data signals with Lorentzian curves, Prony's method or Pisarenko method.

An analyzer in accordance with any of the preceding or hereafter described aspects, wherein the processor is operable to effect damped sinusoidal signal analysis of the sensed data signals; and output a classification of the detected energy as at least part of the output signal based on said signal conditioning.

An analyzer in accordance with any of the preceding or hereafter described aspects, wherein said processor is operable to classify said output signal based on one or more parameters selected from the group consisting of energy wave amplitude, phase, frequency and damping coefficient.

An analyzer in accordance with any of the preceding or hereafter described aspects, wherein said processor is operable to classify said compared data based on one or more input patient parameters selected from the group consisting of age, sex, weight, and smoker status.

An analyzer in accordance with any of the preceding or hereafter described aspects, wherein said pulsed force generator includes a motor and selectively displaceable member, the motor being operable to activate the member in a reciprocal movement between a forward impact position, where said member is moved into engagement with said target area or a plessimeter to transmit said pulsed force thereto, and a rearward position wherein the member is moved to a position spaced from said target area.

An analyzer in accordance with any of the preceding or hereafter described aspects, wherein the motor is operable to activate the piston member in pulsed movement to provide said pulsed force as a pulsed impact force at said target area or at a plessimeter selected at between about 0.1 and 10N, preferably 0.2 to 5N, and preferably 0.5 to 4N, and wherein said member is moved from said rearward position to said forward position, and then from said forward position to said rearward position at a repetition frequency selected between 0.1 and 10 hertz, and preferably between 1 to 2 hertz.

An analyzer in accordance with any of the preceding or hereafter described aspects, wherein the electromechanical actuator is operable to exert a pulsed force at said target area or at a plessimeter by means of electromechanical or other type of energy conversion without using kinetic energy of a moving impactor, wherein said pulsed force is in between about 0.1 and 10N, preferably 0.2 to 5N, and most preferably 0.5 to 4N, and wherein the pulse repetition frequency is selected between 0.1 and 10 hertz, and preferably between about 1 to 2 hertz.

An analyzer in accordance with any of the preceding described aspects wherein the surface vibration or return energy waves detected comprise low frequency vibrations or waves having a frequency of less than 1000 Hz, preferably less than 600 Hz, preferably from about 20 Hz to 300 Hz, and most preferably from about 20 Hz to about 100 Hz.

An analyzer in accordance with any of the preceding or hereafter described aspects, wherein said processor is operable to classify the output signal whereby, signal classification parameters for the analyzer are pre-stored in memory, associating a multi-dimensional vector quantity to the sensed data signals, the vector quantity comprising pre-identified vector coordinates selected from the group consisting of signal amplitude, phase, frequency and damping factor, comparing the associated multi-dimensional vector quantity with one or more preselected signal classification parameters, and outputting said out signal based on the comparison.

BRIEF DESCRIPTION OF THE DRAWINGS

Reference may now be had to the following detailed description taken together with the accompanying drawings in which:

FIGS. 1a and 1b illustrate schematically a portable analyzer for identifying and/or diagnosing a pulmonary or abdominal condition in a patient, in accordance with a preferred embodiment of the invention;

FIG. 12 shows schematically a sample graphic output of an exemplary typical measured percussion and reflected energy signals corresponding to an abdominal air condition, and a generated analytical signal reconstructed from a single damped harmonic mode.

DETAILED DESCRIPTION OF THE PREFERRED EMBODIMENTS

Figure 2:
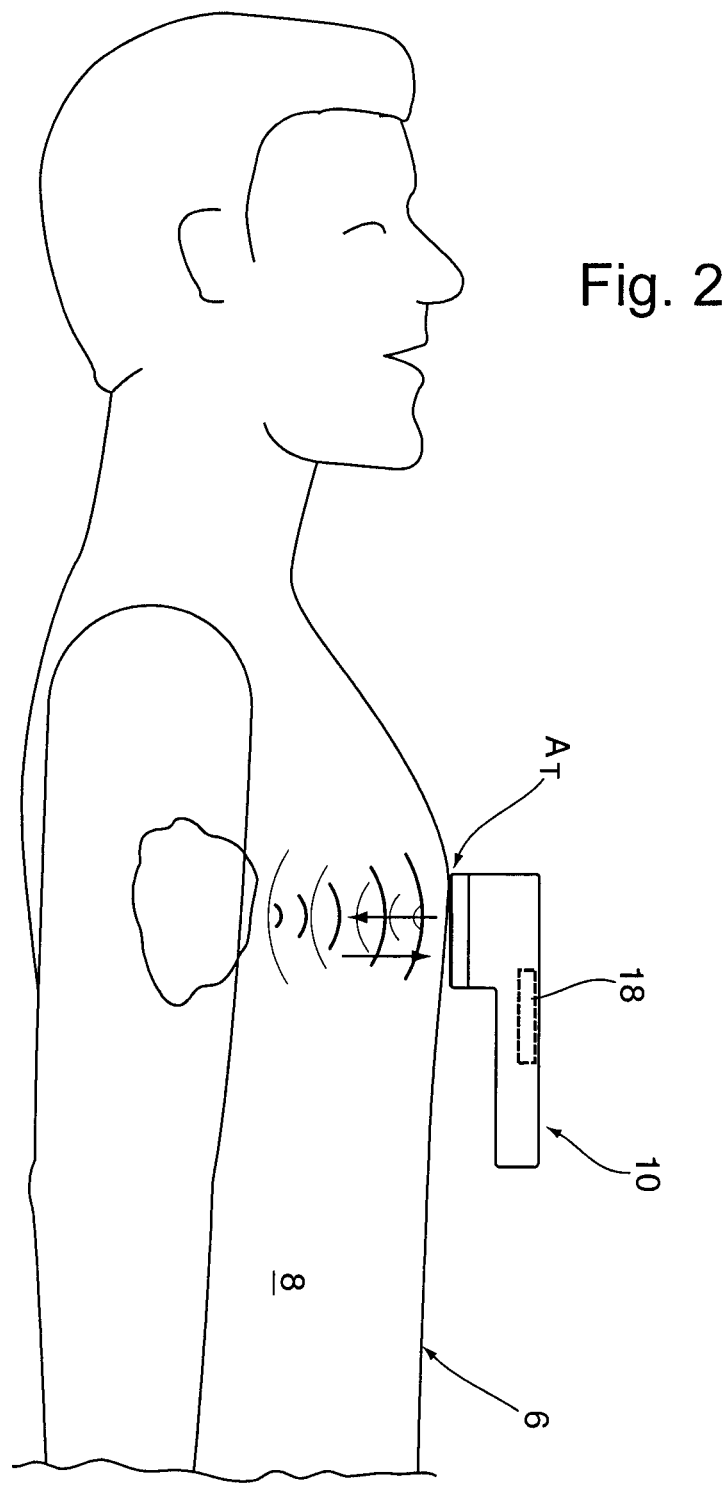
FIG. 2 illustrates schematically the use of the analyzer shown in FIG. 1a in the diagnosis of a potential pulmonary injury in the patient, in accordance with a preferred method of the invention.

The following description describes a preferred embodiment of the invention and is used for descriptive clarity and is not intended to limit the application and use of the invention.

Reference may be had to FIGS. 1a and 1b which illustrate a portable diagnostic device or analyzer 10 used in the diagnosis of a potential pulmonary injury or condition in a patient 6 (FIG. 2) in accordance with a preferred embodiment of the invention. As will be described, the analyzer 10 is operable to generate and impart mechanical disturbance as an output pressure wave (shown as 100 in FIG. 5) or force on the patient's chest 8; and then detect and analyze the surface vibrations or the return reflected wave (shown as 150 in FIG. 6) produced thereby.

As shown in FIGS. 1a and 1b, the analyzer 10 includes a pulsed force generator 12, for generating the output pulsed force, a sensor assembly 14 for detecting return wave energy 150 and converting the detected energy into electric signals, a processing assembly 16 and an output display 18 which is operable to output to a user, a visual graphic output 20 identifying the absence and/or presence of a potential pulmonary and/or abdominal condition under test. Optimally, the analyzer 10 may be further operational to output via the display 18 both instructions regarding the initial placement and operation of the analyzer 10, as well as directions as to possible treatment and patient care, having regard to any condition or trauma identified.

Figure 3:
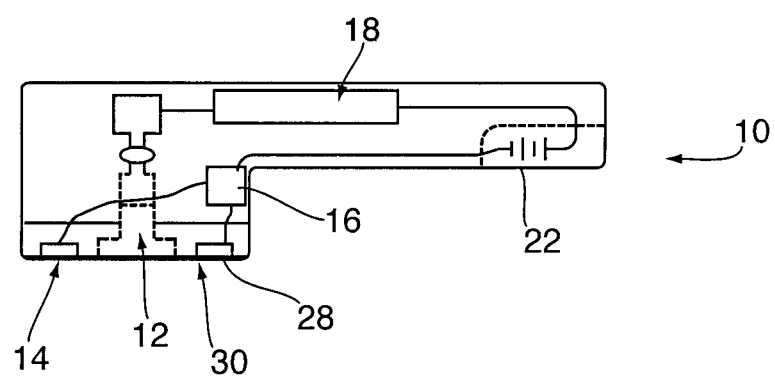
FIG. 3 shows schematically a sectional view of the analyzer shown in FIG. 2.

As shown in FIGS. 2 and 3, the analyzer 10 is adapted for portable use and includes an internal battery power supply 22 which is used to provide electrical power to the pulsed force generator 12, sensor assembly 14 and processing assembly 16. The processing assembly 16 electronically communicates with each of the pulsed force generator 12, sensor assembly 14 and output display 18 and, as shown in FIG. 4, includes memory 24 and a central processing unit (CPU) 26 for receiving and storing data signals from the sensor assembly 14 and the pulsed force generator 12.

Figure 4:
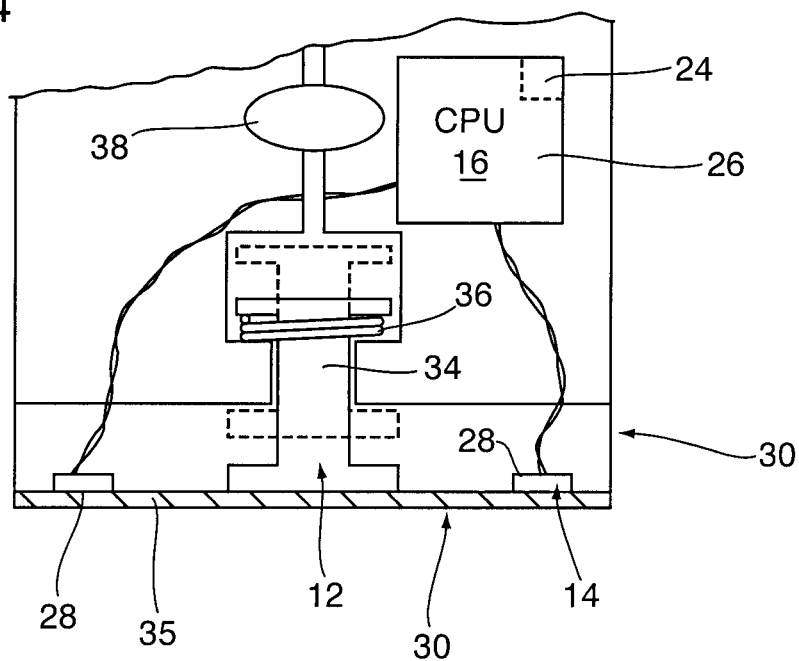
FIG. 4 shows an enlarged cross-sectional view of the pulsed force generator and sensor assembly used in the analyzer of FIG. 2.

FIGS. 1a and 4 show best the sensor assembly 14 as including a number of acoustic transducers 28. The transducers 28 are positioned in a circularly extending array about the periphery of an analyzer sensing head 30 which is adapted to be placed in direct juxtaposed contact against a selected target area $A_T$ of the patient's chest 8. Each of the acoustic transducers 28 is configured to detect and transmit to the CPU 26 data signals representative of sensed reflected return energy waves 150.

Figure 5:
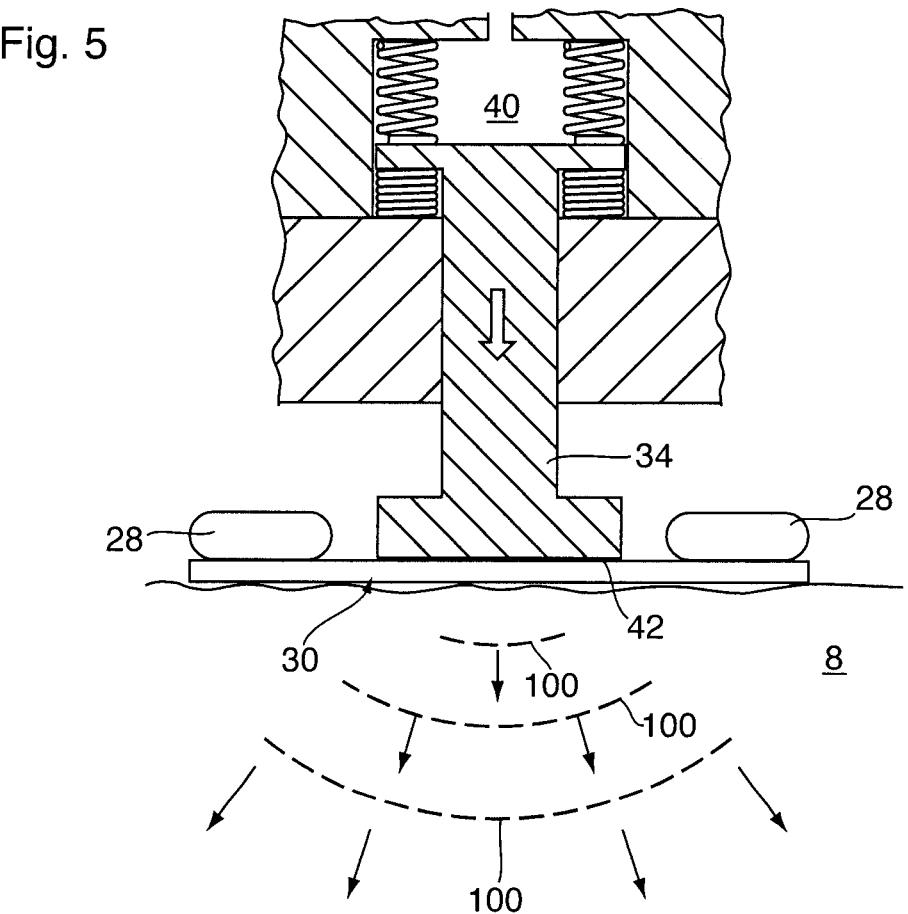
FIG. 5 illustrates the forward displacement of the energy generator piston in the output of a pulsed force into the patient's chest cavity.
Figure 6:
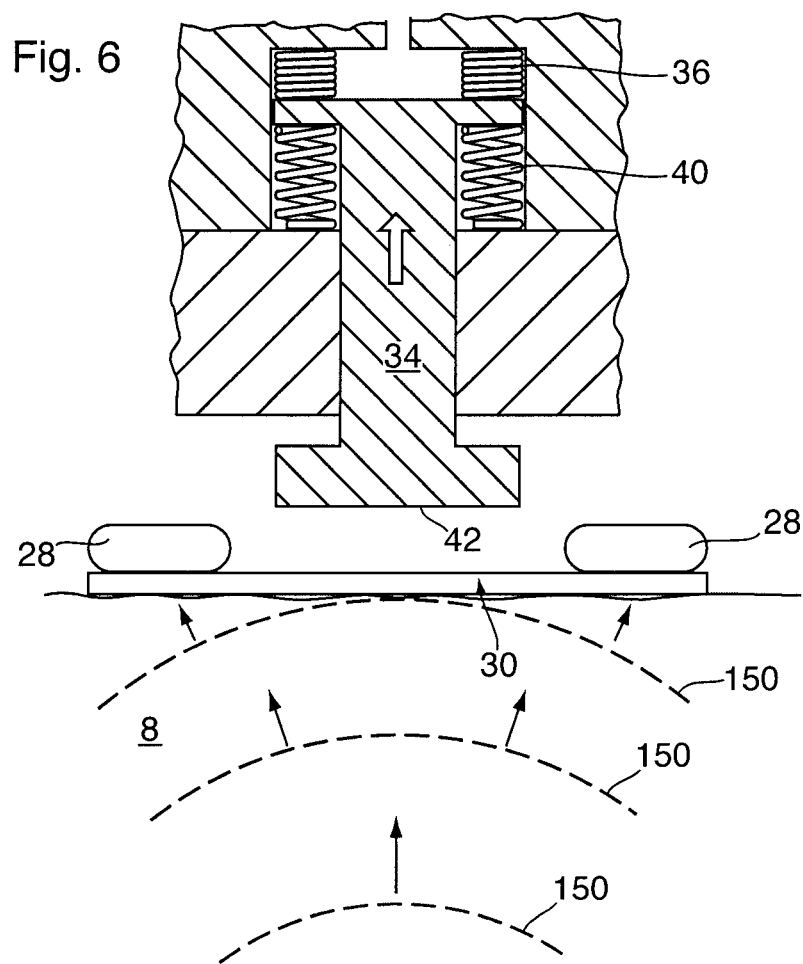
FIG. 6 illustrates schematically the positioning of the pulsed force generator piston in a retracted position during the sensing of reflected return energy waves.

FIGS. 4 to 6 illustrate best the pulsed force generator 12 and its operation in generating at the target area $A_T$ on the patient's chest 8 the output pulsed force 100.

The pulsed force generator 12 includes an electro-mechanically displaceable piston 34 which is engagable with a plessimeter 35, a resiliently deformable biasing spring 36 and a selectively operable electro-magnet 38. As shown best in FIGS. 5 and 6, the piston 34 is reciprocally moveable within a piston chamber 40 between the forward impact position contacting the plessimeter 35 shown in FIG. 5, wherein the forward most end 42 of the piston 34 is moved into engaging contact there against, whilst the plessimeter 35 is pressed against chest 8 at the target area $A_T$; and the retracted position shown in FIG. 6, where the piston 34 is moved with its forward end 42 spaced rearwardly therefrom.

When activated, the electro-magnet 38 operates to move the piston rearwardly against the bias of the spring 36 to the retracted position shown in FIG. 6. In operation of the analyzer 10, the electro-magnet 38 is selectively cycled to release the piston 34 so as to move rapidly under the force of the spring 36 into contact against the patient's chest 8, thereby generating at the target area $A_T$, an output initial pulsed force 100 of between about 0.5 and 4N, and with a frequency of up to 10 Hz, and preferably 1 to 2 Hz. The pulsed force generator 12 is operable to produce and generate an output pulsed force 100 which is sufficient to generate at the target area $A_T$ one or more return energy waves 150 which are detectable by the analyzer sensor assembly 14, having regard to the particular pulmonary and/or abdominal condition under test.

Although not essential, in a most preferred mode of operation, the pulsed force generator 12 is operable to output to the patient 6 a preselected output pulsed force 100 and which optionally, may vary having regard to the specific target area $A_T$ of analyzer use on the patient's chest and/or abdomen.

The pulsed force generator 12 is preferably operable to impart at the target area $A_T$ a mechanical force having a preselected, and most preferably consistent magnitude. In an alternate embodiment, the analyzer 10 may allow for variable adjustment in the output force 100 applied to the patient 6, depending on subjective factors such as the user's body type, age, or weight, and/or depending on the specific use site of the analyzer 10.

Following the activation of the pulsed force generator 12, activation of the piston 34 and impart into the patient's chest 8 the output energy wave 100, the sensor assembly 14 is operated to detect one, and preferably a number of return energy waves 150 which are generated within the patient's chest 8 by the activation of the piston 34.

Most preferably, the acoustic transducers 28 electronically transmit signals to the CPU 26 and memory 24. The CPU 26 operates with the memory 24 to effect signal detection conditioning and damping, and to output via the display 18 a visual signal analysis. In this regard, the analyzer 10 may be used in the automated generation and analysis to effect the unbiased diagnosis of pulmonary trauma or disease. Furthermore, by the use of consistent automation, the analyzer 10 advantageously eliminates subjective factors associated with the conventional, manual percussion diagnosis, allowing the analyzer 10 to be used in the field by non-medical or casually-trained professionals.

Figure 7:
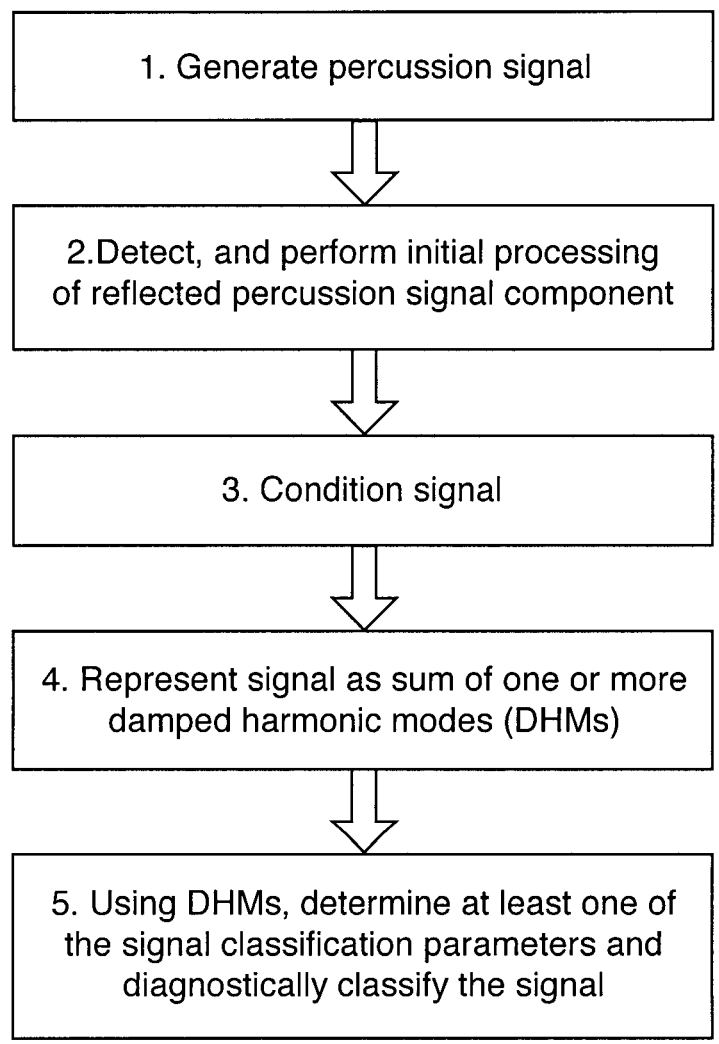
FIG. 7 illustrates a flow chart describing the operation steps of the analyzer shown in FIGS. 1a and 1b in accordance with a preferred method of operation.

As shown in FIG. 7, the analyzer 10 is operated to perform each of the steps of producing or generating the initial output pulsed force 100 or percussion signal, and therefore sensing and detecting the return energy waves 150 which are produced by the initial wave energy 100 reflecting and/or transitioning through patient organs, fluids and/or bones. The step of generating the output pulsed force 100 or percussion signal, and detecting and performing initial processing of the reflected return energy waves 150 as pulmonary or abdominal percussion signals produced thereby, most preferably includes a number of sub-steps. These include effecting the initial mechanical disturbance or force transfer of a selected pulsed force at the target area $A_T$ surface of the chest 8 of the patient 6 under examination; detecting the return energy waves 150 reflected as percussion signals generated internally by the transfer of output pulsed force 100 to patient organs thereby; converting the detected return energy waves 150 into electrical signals; and using the CPU 26, selecting an informative (carrying useful diagnostic information) portion of the signal.

As described, the initial percussion is performed using portable pulmonary injury diagnosis analyzer 10, with the piston 34 operable to impact the target area $A_T$ of the patient's chest 8 with a preselected pulsed force.

The initial step of producing the mechanical disturbance at the surface of the patient's chest 8 generates a response from the underlying organs and tissues, which effects the generation of return and reflected wave energy 150. The return wave energy signal will have a natural resonant frequency(ies), which is(are) dependent on organ/tissue anatomy and physical condition. Most preferably the return wave energy signal includes a low frequency vibration or wave energy component having a frequency less than 1000 Hz, preferably less than 600 Hz, and preferably ranging from about 20 to 100 Hz. The internally generated signals are detected with the acoustic transducers 28, and converted to analog percussion signals.

The sub-step of detecting return wave energy signals produced by the output disturbance preferably includes receiving and detecting the reflected return energy waves 150 with the sensors assembly 14, and recording the generated signal in the device memory 24. The return energy waves 150 typically will consist of vibrations of external and/or internal organs and tissues produced by the mechanical disturbance.

Figure 8:
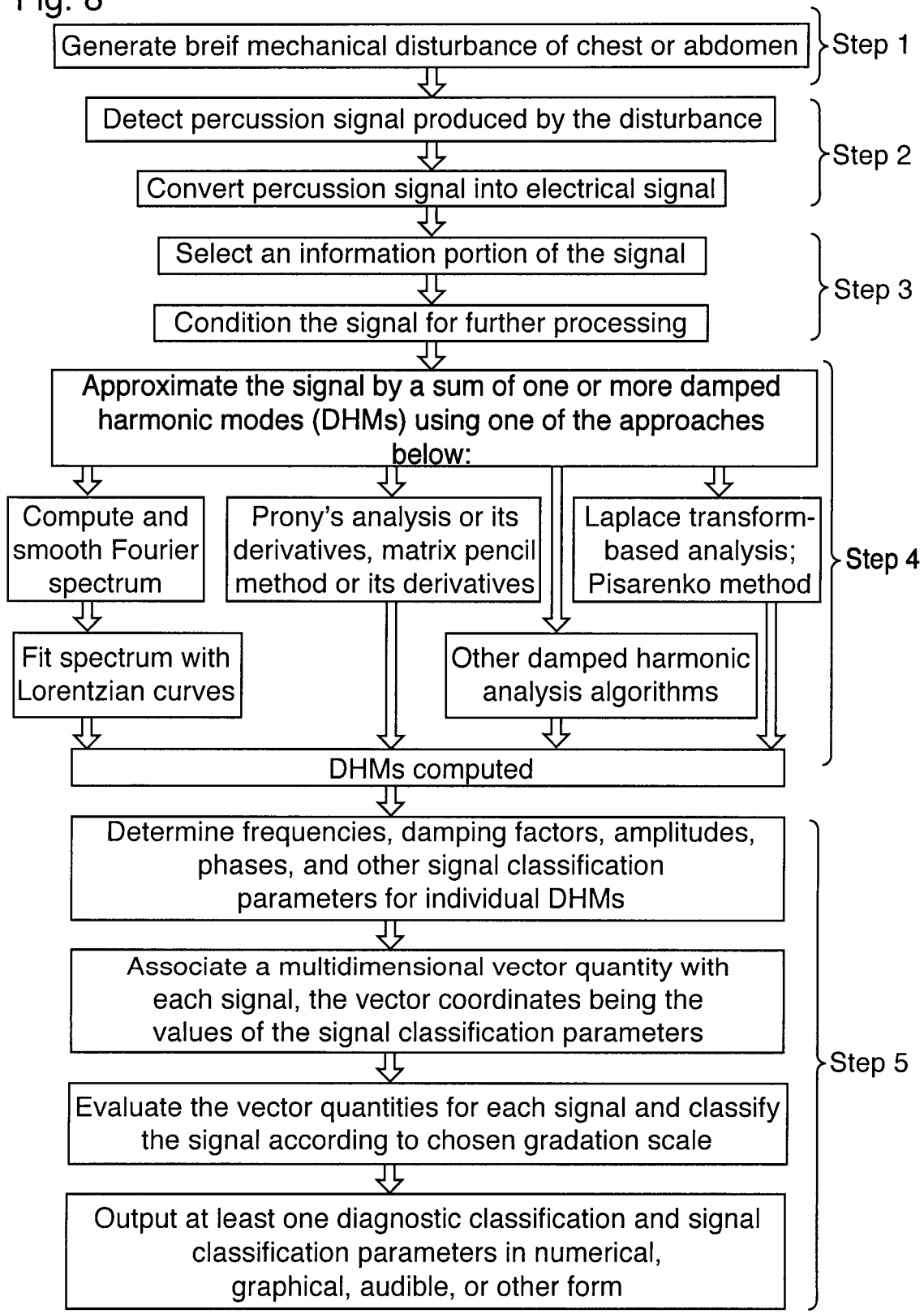
FIG. 8 shows a flow chart illustrating the operation of the analyzer shown in FIG. 2 in detecting and analyzing reflected return energy sensed in the identification and/or confirmation of the presence or absence of a pulmonary disease and/or condition.

As shown in FIG. 8, preferably the analyzer CPU includes stored programme instructions for operations by the use of damped harmonic analysis of the sensed return wave/vibration in the automated diagnosing of pulmonary and abdominal injuries. In a preferred mode, the analyzer 10 performs the step of generating the output mechanical force or disturbance to the patient's chest 8 by percussion to effect transmission of the predetermined and preselected pulsed force 100. The exertion of pulsed force to the patient's chest cavity 8 in turn results in the generation vibrations 150 by the subject's organs as the input disturbance 100 passes therethrough. According to a preferred method, the vibrations/reflected waves 150 generated by organs and/or tissues in the patient's chest 8 or abdomen in response to the input mechanical disturbance 100 are detected by the sensor assembly 14 and transmitted to the CPU 26 for initial processing.

In the CPU 26 conditioning the signal is further performed. Preferably, data representing the sensed vibration/wave signal as a sum of one or more damped sinusoids (herein damped harmonic modes (DHMs)); and the DHMs are used to classify the signal and output signal classification parameters. More preferably, the analyzer memory 24 stores a number of separate predetermined signals which are representative of a signal indicating a normal or optimum physical state, and/or signals which are indicative of a compromised stressed or injured state which for example could represent as particular trauma, disease or other condition. Depending upon the results of the comparison, the CPU 26 may thus be used to activate the output display 18 to illustrate to the user a particular visual graphic display 20 correlated to the most proximate condition pre-stored within the memory 24.

The step of conditioning the detected return energy wave signal preferably includes the sub-steps of: selecting an informative portion of the signal; and preparing the signal for the damped harmonic analysis. Selecting the informative portion of the signal includes examination of the digitized signal in order to identify one or more of its parts containing information about the response of the patient's body to the percussion event. Once identified, the informative portion is separated from the rest of the signal, and the separated portion is used as "the signal" during subsequent processing steps. Typically the identification of the information portion of the signal is performed by filtering and/or signal truncation. In a simplified method, the detected return energy wave is filtered with respect to pre-identified known background parameters.

The sub-step of preparing the signal for damped harmonic analysis may include increasing or decreasing the number of samples in the signal, windowing the signal, removing direct current (DC) offset from the signal, and filtering the signal. Filtering of the signal may remove at least one of undesirable low frequency components and undesirable high frequency components. The conditioned signal may be either kept in the computer memory 24 for further processing or recorded externally using a hard drive, flash memory, or any other suitable storage medium (not shown).

The step of representing the signal as a sum of one or more DHMs is preferably carried out by means of an appropriate damped harmonic analysis algorithm. Each DHM is a damped sinusoid—an analytical function completely defined by its four parameters: amplitude, phase, frequency, and damping. The combination of these parameters for all DHMs representing the signal provides complete information about the signal and may be used, either fully or in its part, for the signal classification and diagnostic purposes. Examples of possible damped harmonic analysis algorithms include, but are not limited to, the nonlinear spectral fitting with multiple Lorentzian curves, Prony's damped harmonic analysis algorithm and its derivatives, the matrix pencil method, signal approximation by single or multiple DHMs derived from the spectral envelope, the Pisarenko method, the approach based on finding coordinates of the poles of the complex Laplace transform of the signal, or any other appropriate algorithm capable of representing the signal as a sum of damped sinusoids.

The step of representing the signal as a sum of one or more DHMs may be effected by either analog or digital decomposition of the signal into a sum of one or more damped sinusoids defined by their respective amplitudes, phases, frequencies and damping coefficients. This decomposition may be either exact or approximate. In the case of approximate decomposition, the error may be described in terms of the difference between the actual signal and the signal represented as a sum of one or more DHMs. The error may be evaluated to judge an accuracy of the damped harmonic analysis performed on each particular signal.

Figure 9:
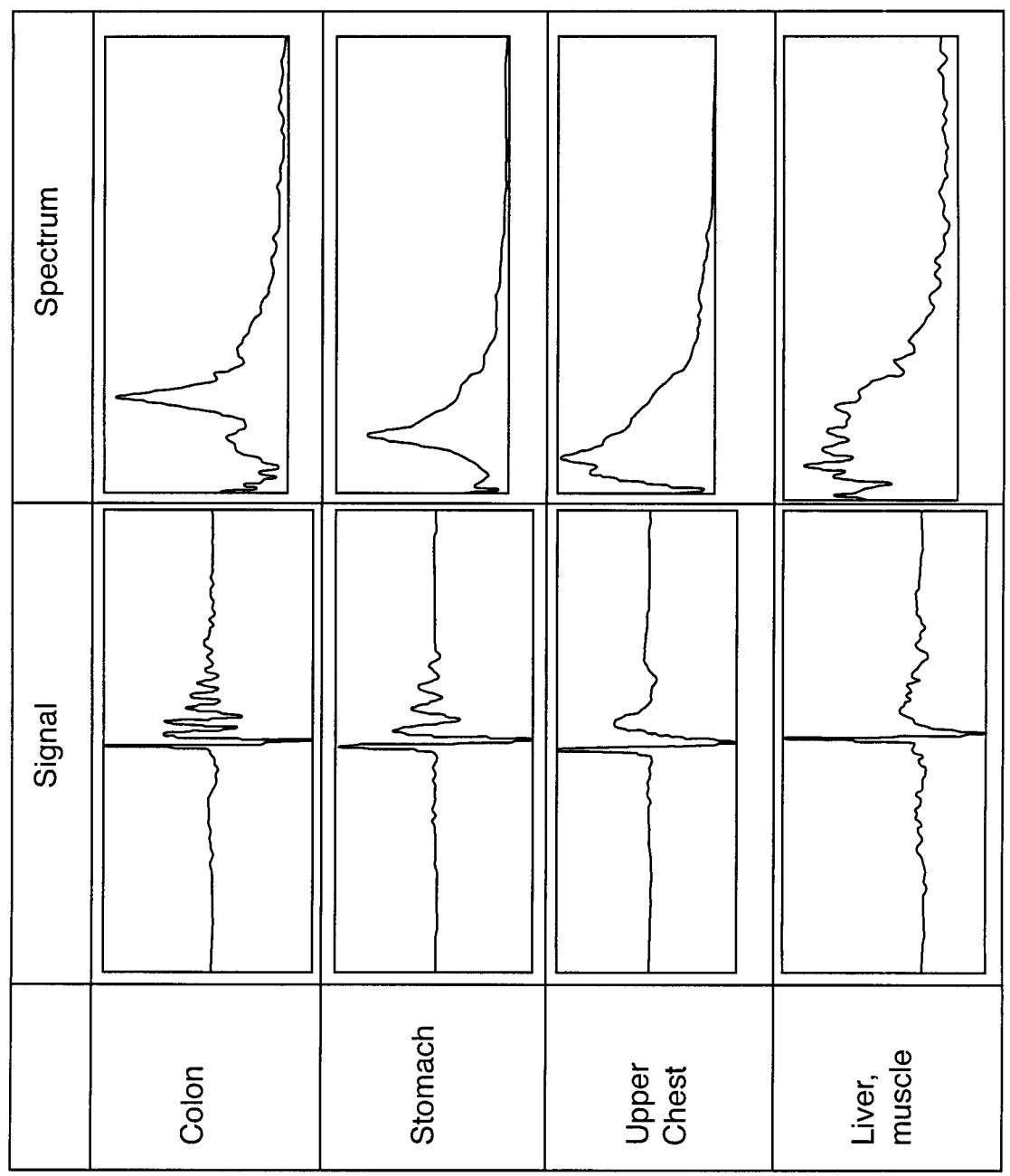
FIG. 9 illustrates graphically sample signal wave forms and spectrum of initially output and sensed pressure waves generated at the patient's colon, stomach, upper chest, liver, and muscle tissues.

If a Fourier spectrum-based algorithm is used for the step of representing the signal as a sum of one or more DHMs, a Fourier Transform may be performed on the signal, producing a frequency spectrum. The frequency spectrum may further be smoothed. FIG. 9 shows exemplary conditioned waveforms and spectra of sensed return energy wave signals generated from different chest and abdominal areas. Peaks of the frequency spectrum may then be determined. A suitable curve-fitting procedure may be used to approximate the determined frequency peaks. Preferably but not exclusively, a set of Lorentzian curves may be used to carry out the fitting process, with each curve representing the spectrum of an independent exponentially damped harmonic oscillator. The amplitudes, peak frequencies f and widths at half height (WHH) w of the Lorentzian curves may be determined according to a selected curve-fitting procedure, thereby concluding the decomposition of the signal into a set of DHMs. (The damping constant of the oscillator corresponding to each DHM b=w/2.) FIGS. 10 to 13 illustrate this approach by examples of two typical percussion signals.

Figure 10:
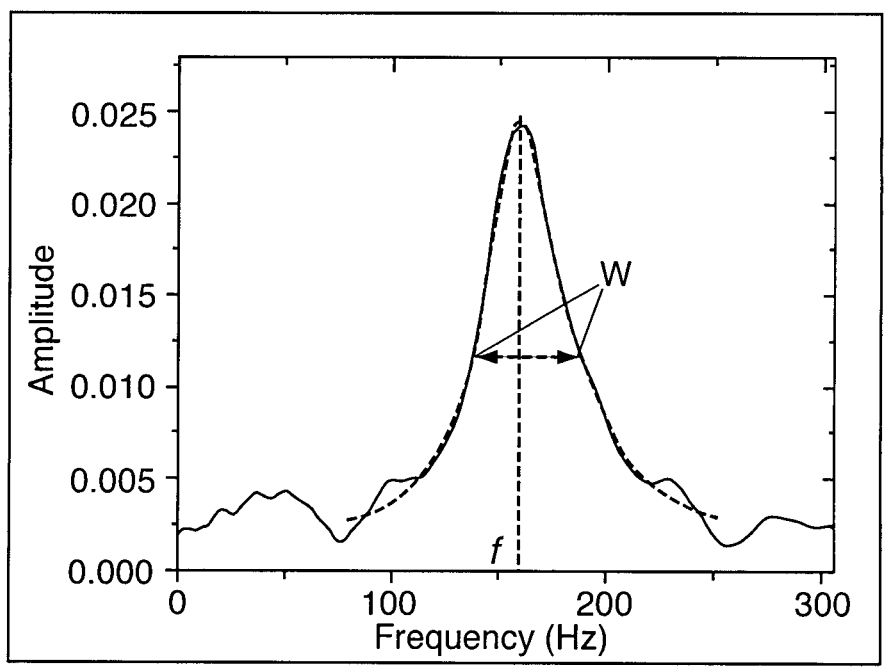
FIG. 10 illustrates graphically a case where one Lorentzian curve provides adequately close fitting of a signal's Fourier power spectrum.

FIG. 10 provides an illustrative example of a typical Fourier spectrum of an abdominal air signal (the solid line) recorded by the system. In this case, one Lorentzian curve (the dashed line) with the peak frequency f and the WHH w suffices to provide adequately close fitting of the main spectral peak.

Figure 11:
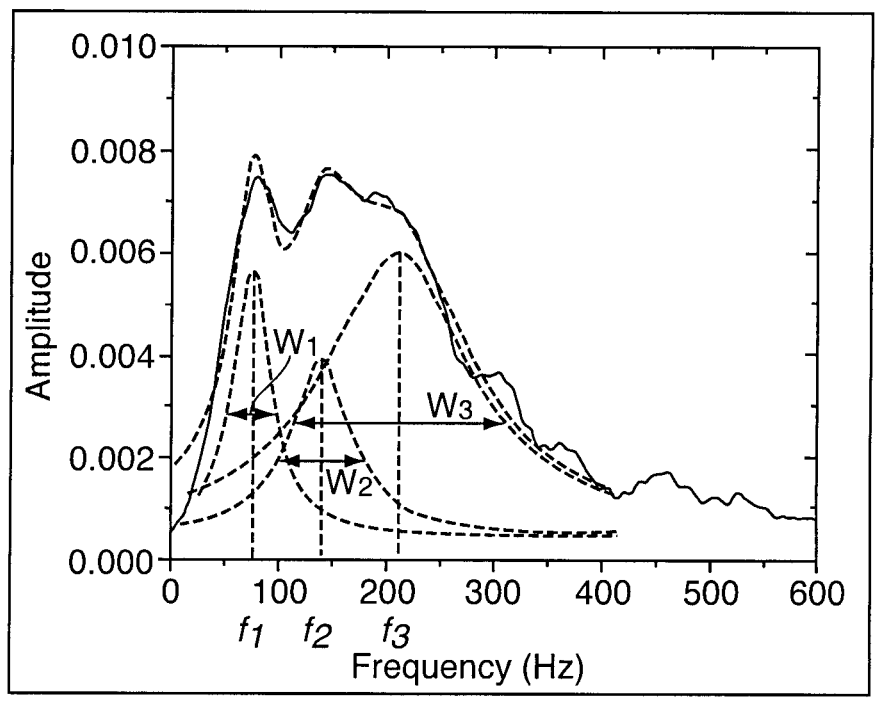
FIG. 11 illustrates graphically a case where three Lorentzian curves provide adequately close fitting of a signal's Fourier power spectrum.

FIG. 11 provides an illustrative example of a typical Fourier spectrum of a pre-identified normal upper chest signal recorded by the system and stored in memory 24. In this case, three Lorentzian curves (the dotted lines) with peak frequencies $f_{1-3}$ and the associated WHH $w_{1-3}$ provide adequately close fitting of the signal spectrum.

Figure 13:
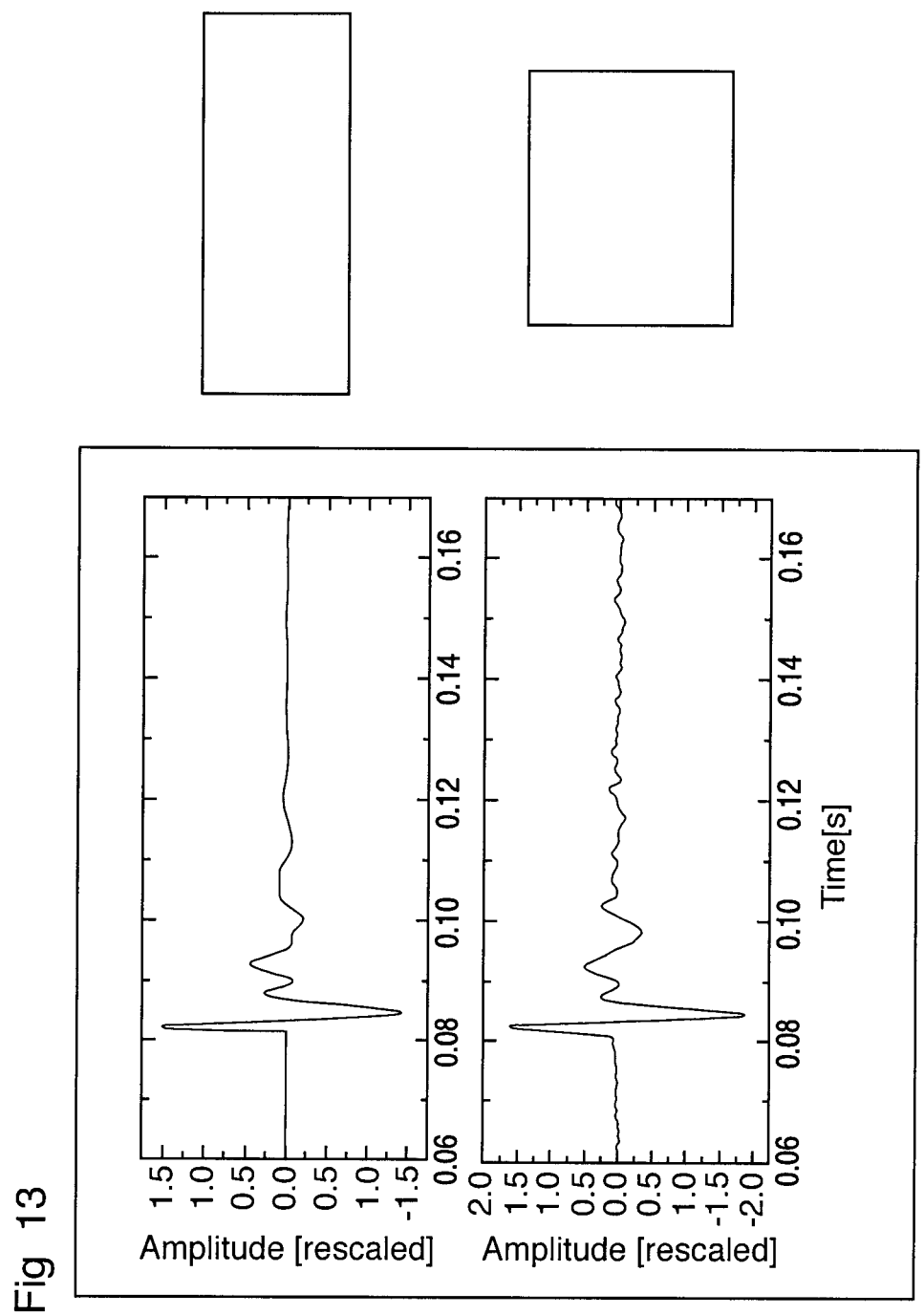
FIG. 13 shows schematically a sample graphic output of an exemplary measured percussion and reflective signals from the patient's upper chest region, and a sample generated analytical signal reconstructed from three damped harmonic modes of the invention.

FIG. 12 shows that the analytical signal reconstructed from a single DHM (bottom graph) closely matches the original abdominal air signal recorded by the system (top graph). FIG. 13 shows that the signal reconstructed from three DHMs (bottom graph) closely matches the original upper chest signal (top graph) recorded by the system. In this case, the amplitudes of the DHMs were derived from the amplitudes of the corresponding Lorentzian curves, while phases were found by a separate reconstruction program. In the preferred embodiment, all four parameters for each DHM may be determined automatically by the damped harmonic analysis algorithm.

If the spectral envelope-derived single damped harmonic mode is used for the step of representing the signal as a sum of one or more DHMs, then the signal is approximated by a single damped sinusoid that is derived from the parameters of the spectral envelope. According to this approach, the damped frequency $\Omega$ is equal to the peak frequency, and the damping factor b equals half the WHH of the spectral envelope. For example, each set of waveforms and spectra shown in FIG. 9 has a distinct (relative to the other waveforms and spectra) combination of $\Omega$ and WHH of the single major spectral peak, which may be used as a signal classifier either alone or combined with additional spectral or time-domain parameters.

If Prony's analysis or any of its derivative algorithms, or the matrix pencil method is used for the step of representing the signal as a sum of one or more DHMs, then the frequencies, damping factors, amplitudes, and phases may be computed for the individual DHMs.

If a complex Laplace transform is used for the step of representing the signal as a sum of one or more DHMs, then the real and imaginary coordinates of the poles of the complex Laplace transform of the signal may be computed for the one or more DHMs. The frequencies may then be identified as the real coordinates of the poles of the complex Laplace transform, while the damping factors may be identified as the imaginary coordinates of the poles of the complex Laplace transform. Alternatively, the Pisarenko method or any other damped harmonic analysis algorithm may be used for the step of representing the signal as a sum of one or more DHMs.

The fourth step of classifying the signal and outputting at least one of the signal classification parameters preferably includes the sub-steps of: computing signal classification parameters for the DHMs; associating a multidimensional vector quantity with each signal, the vector coordinates being the values of the signal classification parameters; evaluating the vector quantities of each signal and classifying the signal as one or more of "tympanic," "resonant," and "dull"; or using a different gradation scale; and outputting at least one of the diagnostic classification and the signal classification parameters in numerical, graphical, audible, or other form.

Signal classification parameters for each DHM include amplitude, phase, frequency, and damping factor. Additional classification parameters for each DHM may include damped frequency $\Omega$ and quality factor Q. Supplementary classification parameters derived from the signal waveform may include number of oscillations, number of zero crossings, zero-crossing rate, temporal envelope width at selected threshold levels, and other time- and frequency-domain parameters. The step of computing signal classification parameters from the DHMs may be carried out according to any acceptable method known in the art. The results of the damped harmonic decomposition of the signal may thereby be processed to reconstruct the main modes of the signal. The process produces quantitative information that may be used as a distinctive classifier of percussion signals and may be represented in a graphical, numerical, audible, or other form to facilitate interpretation by an examiner.

The sub-step of associating a multidimensional vector quantity with each signal is carried out based on the fact that the vector coordinates correspond to the values of the signal classification parameters. The sub-step of evaluating the vector quantities of each signal and classifying the signal results in attribution of the signal to one or more of the three conventional categories of acoustic signals, "tympanic," "resonant," and "dull". Such simple classification, for example, could be useful for rapid identification of severe pulmonary conditions, such as pneumothorax, where a "tympanic" signal detected in the upper chest region instead of a typically observed "resonant" one would indicate the presence of anomaly. A more refined gradation of the signals, based on the values of the above vector quantities, is also possible with this method and can be used to build diagnostic images in cases when detailed percussion examinations are performed. The sub-step of outputting the signal classification parameters may be carried out by a numerical or text display, a graphical display, an audible output, or any other form of output intelligible to an examiner.

The analysis and classification of pulmonary and abdominal percussion signals utilizes a model based on the general concept of a multi-mode exponentially damped harmonic oscillator that, besides the abdomen, may be applied to both upper chest and lower chest percussion. The system is preferably configured to decompose an arbitrary percussion signal into a sum of a small number of damped sinusoids called here damped harmonic modes (DHM) with corresponding amplitudes, frequencies, phases, and damping factors. These parameters combined fully define the original signal and therefore can be used for classification purposes. For example, a combination of two of the parameters associated with each DHM, namely, quality factor Q and the damped frequency $\Omega$, has been experimentally found to have high diagnostic classification potential. As shown in FIGS. 10 to 13, a general percussion signal may be represented as a sum of a small number of DHMs, each representing a particular oscillating subsystem. Since only a few DHMs are required to represent the signal, this is an advantage over conventional Fourier analysis where a much larger number of infinite-duration sinusoidal waves is used for the same purpose. Accordingly, real chest percussion signal may be synthesized from several damped oscillator modes that were extracted from it according to embodiments of the invention.

It is envisioned that the analyzer 10 of the present invention may be used in a variety of differing operational modes and/or applications. In one possible mode of operation, the actuator 12 may be operated to transmit pulsed or disturbance forces to the patient using comparatively low frequency signals, as for example, at a rate of 1 to 100 beats or impact forces per minute, whilst the sensor assembly 14 may be selected to detect return percussion signals in a less than 0 to 600 Hz range, which correlates to either a natural frequency or harmonic of the patient's internal organs and/or body parts. The analyzer 10 may further be operable to utilize a damped harmonics mode and/or analysis to determine the return signal frequency, amplitude, phase, and/or other signal classifications.

More preferably, the device processing assembly 16 is selected to separate individual signals from a mixed return signal and/or provide signal recognition and referencing correlated to selected patient organs. The processing assembly 16 may furthermore store a map of base signals used to parse, recognize and/or analyze mixed return signals generated in the patient's chest/torso. It is to be appreciated that by the use of handheld portable device 10, the device may be operated in a non-evasive manner as a method of determining the condition of pulmonary function for human, veterinary or other animal use.

In other non-limiting constructions, however, the apparatus could operate to generate a pressure wave by the use of air and/or gas pressure, electric stimulation, or other physical impact devices, while the preferred embodiment describes the sensor assembly 14 as including acoustic transducers 28, the invention is not so limited. In another possible embodiment, the signals generated by return waves 150 may be detected using other acoustic and/or audio sensors which convert the detected energy into sensed electric data signals. Such sensors would include other types of non-contact sensors, such as air microphones, laser vibrometers, and other suitable non-contact vibration or pressure sensors. Alternatively, the return energy waves 150 may be detected using direct contact pressure sensors or other suitable apparatus, including, for example, a microphone embedded into a stethoscope head, a contact accelerometer, a piezofilm sensor, or any other suitable contact vibration or pressure sensor. The sub-step of converting the generated return energy wave signal into electrical signals also include amplifying and preconditioning, for example, by analog filtering, an analog return percussion signal. In an alternate embodiment, the signal may be preprocessed, as for example, by digitizing the output percussion signal and/or one or more detected return energy waves.

Although the preferred embodiment describes the analyzer 10 as having an internal processor assembly 16, the detected signals alternating either transferred to computer memory which is external for further processing, or recorded using a hard drive, flash memory, or any other suitable storage medium.

Although the detailed description describes an electromagnetically actuable piston 34 as used to generate the output energy force 100, the invention is not so limited. Other force inducing constructions may also be used. Such generators include other moveable impactors activated by pneumatic, hydraulic, electromechanical, or electromagnetic means. Alternatively, the analyzer 10 may be operable to effect percussion using pressurized fluid sources, such as pneumatic impact or electromechanical sources operable to provide a pulsed force designed to reproduce the effect of percussion impact without the moving impactor.

While the detailed description describes the best mode, the invention is not limited to the described embodiment. In other non-limiting applications, the method and apparatus may also be used in a variety of applications including without restriction, in veterinary diagnostics; material analysis; change of state analysis in multiphase materials; and viscosity analysis of liquids, jells and semisolids.

A person skilled in the art will recognize from the previous detailed description and from the figures and claims, modifications and changes can be made to the preferred embodiments of the invention without departing from the scope of this invention defined in the following claims.

We claim:

1. An analyzer for diagnosing a pulmonary and/or abdominal condition of a patient, the analyzer comprising,
    a pulsed force generator operable to generate and transmit to a target area of the patient at least one preselected output pulsed force, each said output pulsed force being selected to generate at the target area at least one associated vibration or reflected return wave,
    a sensor assembly for detecting the at least one vibration or reflected return wave at said target area, and converting detected energy thereof into electrical signals, memory containing stored data representative of pre-stored vibration or reflected wave profiles indicative of the presence and/or absence of one or more pulmonary and/or abdominal conditions, a processor containing programme instructions, whereby said processor is operable to,
        compare data representative of the detected energy of at least a part of the at least one associated vibration or reflected return wave generated with said stored data representative of at least one said pre-stored vibration or reflected wave profiles and, based on the compared data generate an output signal indicative of a potential presence or absence of a pulmonary disease and/or condition in said patient,
    wherein said processor includes pre-stored software comprising programme instructions operable to compare data representative of an output parameters of said output pulsed force and the data representative of the detected vibration or reflected waves,
    perform damped harmonic analysis on at least one of said data representative of said output disturbance and said data representative of said detected vibration or reflected waves, and
    wherein said damped harmonic analysis comprises non-linear spectral fitting of the detected energy of a plurality of said associated return energy waves detected at the target area, with at least one of Lorentzian curves, Prony's method and Pisarenko method.

2. The analyzer as claimed in claim 1, wherein the processor is operable to identify and select, by at least one of signal filtering and signal truncation, an informative portion of the electrical signals as the part of the at least one associated return energy wave compared with said stored data.

3. The analyzer as claimed in claim 2, wherein the informative portion of the detected energy is identified and selected by filtering the electrical signals based on pre-identified background patterns.

4. The analyzer as claimed in claim 1, wherein the processor is operable to effect damped sinusoidal signal conditioning on data, representative of the detected energy of at least part of a plurality of said detected vibrations or reflected return waves; and output a classification of the detected energy as at least part of the output signal based on said signal conditioning, and wherein prior to damped harmonic analysis, the processor is operable to effect signal conditioning of the detected energy electrical signals by one or more steps selected from the group consisting of windowing the electrical signals, removing direct current (DC) offset from the electrical signals; and filtering preselected high and/or low frequency components from the electrical signals.

5. The analyzer as claimed in claim 1, wherein said processor is operable to classify said output signal based on at least one vibration or reflected return wave parameter selected from the group consisting of wave amplitude, phase, frequency and damping coefficient.

6. The analyzer as claimed in claim 5, wherein said processor is further operable to effect classification of the output signal based on at least one input patient parameter selected from the group consisting of patient age, sex, weight, and smoker status.

7. The analyzer as claimed in claim 1, wherein said pulsed force generator includes a selectively displaceable piston member which is movable between a forward position, where said piston member engages said target area or a plessimeter to transmit said output pulsed force thereto, and a retracted position spaced therefrom.

8. The analyzer as claimed in claim 7, wherein the output pulsed force comprises a pulsed impact force at said target area selected at between about 0.1 and 10N, preferably 0.2 to 5N and more preferably 0.5 to 4N, and said output pulsed force comprises a pulsed impact force having a repetition frequency selected between 0.1 and 10 hertz.

9. The analyzer as claimed in claim 1, wherein said target area is selected from the group consisting of a chest area, a back area and an abdomen area of the patient.

10. The analyzer as claimed in claim 7, wherein said analyzer comprises a portable hand-held pulmonary function tester for diagnosing a pulmonary injury or condition in said patient; said tester further comprising a portable power source for supplying electric power to said pulsed force generator and said sensor assembly, and an output display for displaying said output signal as a graphic output.

* * * * *